United States Patent [19]

Hussin

[11] Patent Number: 5,340,313
[45] Date of Patent: Aug. 23, 1994

[54] TOOTH ISOLATION DEVICE

[76] Inventor: Gregory J. Hussin, P.O. Box 1111, Crystal Beach, Fla. 34681

[21] Appl. No.: 65,615

[22] Filed: May 21, 1993

[51] Int. Cl.⁵ .......................... A61C 5/14; A61C 5/00
[52] U.S. Cl. ........................................ 433/136; 433/140
[58] Field of Search ............... 433/93, 136, 138, 140, 433/215; 128/12, 14, 15, 19, 20

[56] References Cited

U.S. PATENT DOCUMENTS

| | | | |
|---|---|---|---|
| 66,317 | 12/1900 | Kuns . | |
| 770,854 | 9/1904 | Hare | 128/12 |
| 1,159,496 | 11/1915 | Ivory . | |
| 2,092,549 | 9/1937 | Craigo | 32/34 |
| 3,151,394 | 10/1964 | Arroyo | 32/35 |
| 3,396,468 | 8/1968 | Dayhoff | 433/140 X |
| 4,053,984 | 10/1977 | Moss | 128/12 X |
| 4,992,046 | 2/1991 | Sharp | 433/140 X |
| 5,152,686 | 10/1992 | Duggan et al. | 433/140 X |

*Primary Examiner*—Gene Mancene
*Assistant Examiner*—Nicholas D. Lucchesi
*Attorney, Agent, or Firm*—Pettis & McDonald

[57] ABSTRACT

A dental appliance whereby the device isolate particular teeth from the tongue and body fluids within the patient's mouth, captures the residue from the treatment therein and props the patient's mouth open. The device comprises a flexible cup-shaped member comprising a bottom portion and at least one side with at least one aperture formed therethrough. A flexible sealing element comprising a slit therethrough sealingly covers the aperture. The aperture is sized and configured to receive at least one molar through the slit and the adjacent aperture so that the molar is received within the member and the sealing element seals the gap between the tooth and the device.

11 Claims, 1 Drawing Sheet

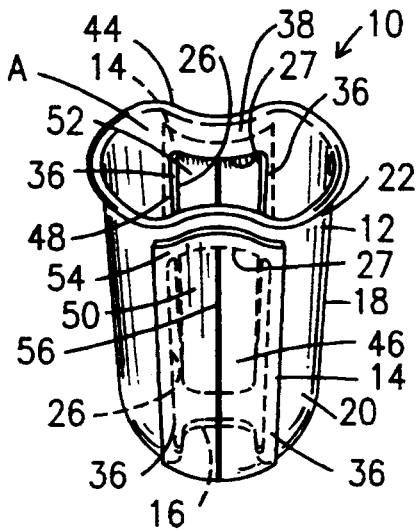
Fig. 1
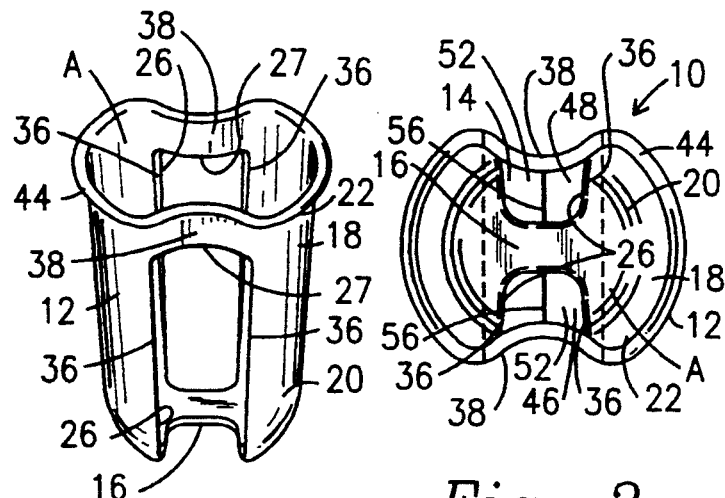
Fig. 2
Fig. 3
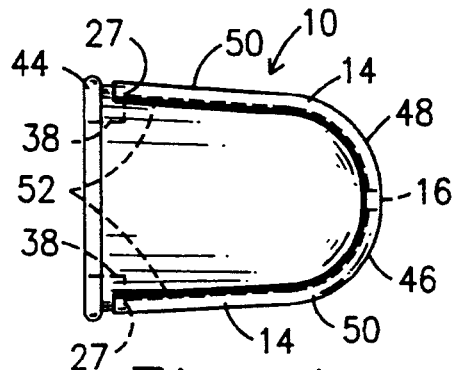
Fig. 4
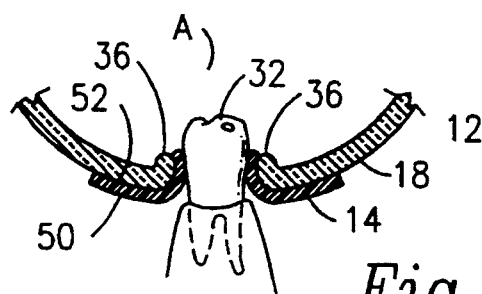
Fig. 5
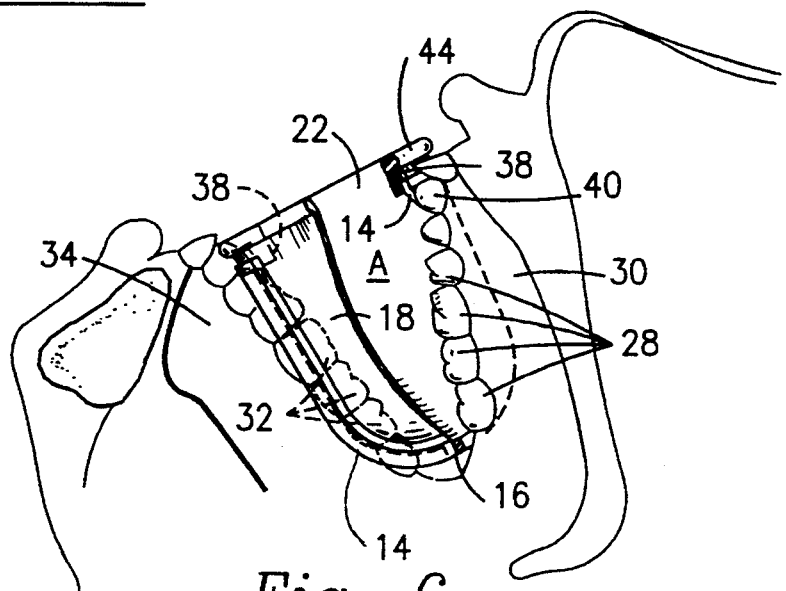
Fig. 6

TOOTH ISOLATION DEVICE

BACKGROUND OF THE INVENTION

1. Field of the Invention

The present invention relates to a dental appliance, more particularly a tooth isolation device, that permits dental work upon one or more teeth while shielding those teeth from the tongue and body fluids within the mouth. In addition, the device captures the residue accumulated during treatment for easy removal by standard dental procedures. The isolation device also provides support to maintain the mouth in a stable open position for easy access.

2. Description of the Prior Art

Dental dams using various techniques to isolate one or more teeth from the surrounding area in the mouth are well known in the art. U.S. Pat. No. 663,178, issued to Nathaniel Kuns, illustrates a metal holder for holding sheet rubber that is inserted over a tooth that is to be worked on. A rubber-dam-clamp is inserted through a perforation through the rubber-dam and the dam and the clamp are then placed over the tooth providing a seal.

U.S. Pat. No. 1,159,496, issued to James Ivory, illustrates a rubber-dam clamp. The clamp comprises a spring frame having a pair of jaws joined together by a spring bridge so that the jaws may be held in place about the teeth. To each jaw is attached a wing over which is wrapped the rubber-dam during placement of the device over the patient's teeth. When the device is in place a rubber-dam is attached to four or more points on the periphery of the wings to form a cup-shaped area.

U.S. Pat. No. 2,092,549, issued to John M. Craigo, discloses various cup-shaped devices composed of a resilient and elastic rubber. In the bottom of the cup are a number of holes for receiving one or more teeth, thereby isolating those teeth from their surroundings.

Notwithstanding the existence of such prior art devices, there is a need for a simple, inexpensive device that provides a means for isolating teeth rapidly and positively from their surroundings, even when the teeth have little or no space between one another or are misaligned. There is a need for a device that also provides support to the patient's jaws so that the jaws are maintained in an open and stable position for easy access.

SUMMARY OF THE INVENTION

The present invention relates to a tooth isolation device whereby one or more teeth are quickly and positively sealed from the surrounding area, while at the same time the upper and lower jaws are maintained in an opened position in relation to one another. The tooth isolation device is particularly adapted for use with upper and lower molars. The device comprises a flexible cup-shaped member having a bottom portion and at least one side that extends outwardly from the bottom portion to define an open end. The member has at least one aperture formed therethrough that extends from the bottom portion along the side of the member to a point near the open end.

A flexible sealing element is attached to the cup-shaped member so that it sealingly covers the aperture. The sealing element has a slit formed therethrough that communicates through the aperture with the interior of the member. When the member is inserted into the mouth of a patient, the aperture is aligned with the molars on one side of the mouth and pressed onto the molars so that at least one molar projects through the slit in the sealing element, through the aperture and into the interior of the cup-shaped member. The sealing element is pressed about the molar and the adjacent gum area so that the molar is isolated from the mouth fluids.

The invention accordingly comprises an article of manufacture possessing the features, properties and the relation of elements which will be exemplified in the article hereinafter described, and the scope of the invention will be indicated in the claims.

BRIEF DESCRIPTION OF THE DRAWINGS

For a fuller understanding of the nature and objects of the invention, reference should be had to the following detailed description taken in connection with the accompanying drawings, in which:

FIG. 1 is a perspective view of a preferred embodiment of the tooth isolation device of this invention.

FIG. 2 is a perspective view of the invention of FIG. 1 with the flexible sealing element having been removed.

FIG. 3 is a plan view of the invention of FIG. 1.

FIG. 4 is a right side elevation view of the invention.

FIG. 5 is a cross sectional view of a portion of the invention illustrating the insertion of a molar through the aperture of the invention.

FIG. 6 is a view of the invention of FIG. 1 that is partially broken away to illustrate the invention in place within the mouth of a patient.

Similar reference characters refer to similar parts throughout the several views of the drawings.

DETAILED DESCRIPTION

A preferred embodiment of the tooth isolation device of this invention is illustrated in the drawing FIGS. 1–6 and is generally indicated as 10. Referring first to the view of FIG. 1, it can be seen that the tooth isolation device 10 comprises a cup-shaped member 12 and a flexible sealing element 14.

In a preferred embodiment shown in FIG. 2, the cup-shaped member 12 comprises a bottom portion 16 and at least one side 18 that extends outwardly from the bottom portion 16. The side 18 has a first end 20 that is joined to the bottom portion 16 and a second end 22 that is spaced apart from the bottom portion 16 defining an open end of the member 12. In a preferred embodiment the side 18 is formed contiguously with the bottom portion 16 to provide a smooth transition between the side 18 and the bottom portion 16. In a preferred embodiment, the member 12 has two apertures 26 formed therethrough, the apertures generally opposing one another. Each aperture is formed through the bottom portion 16 and through side 18 extending along side 18 to a point proximal to the second end 22. Each aperture is wide enough and long enough to receive the molars of the person for whom the tooth isolation device 10 is designed. For comfort and ease of use tooth isolation devices 10 may be made in any number of sizes between the preferred size for a small child and the preferred size for a large adult. In the illustrated embodiment of FIGS. 1–6, the two apertures 26 each extend into the bottom portion 16; however, the isolation device 10 would work satisfactorily if the apertures extended only along the side 18. The two apertures 26 are sized and configured to simultaneously receive upper molars 28 from one side of the upper jaw 30 and lower molars 32 from a corresponding side of the lower jaw 34, as seen in FIG. 6. The longitudinal edges 36 of the apertures 26 curve inwardly in relation to the member 12 so that the edges of the aperture 26 do not scrape the gums of the patient. The spacing between the edges 36 must be sufficient to allow the reception of misaligned molars 28 and 32.

In addition, to provide a better fit in the patient's mouth the member 12 is tapered so that the circumference of the member adjacent the bottom portion is smaller than the circumference adjacent to the second end 22. This permits a deeper insertion into the mouth of the patient toward the hinge point (not shown) of the upper jaw 30 and the lower jaw 34.

A concave segment 38 is formed in the side 18 of member 12 to receive the most forward teeth, usually the eye teeth 40. A concave segment 38 extends between the first end 27 of each aperture 26 to and including a section of the second end 22 of side 18 to provide a generally figure eight appearance, as illustrated in FIG. 3.

In the preferred embodiment, member 12 is comprised of a light-weight, thin and flexible plastic material that is stiff enough to provide a prop between the upper jaw 30 and the lower jaw 34, but yet is flexible enough to allow the apertures 26 to fit about misaligned teeth. In other embodiments, member 12 may be constructed of coated paper or any other suitable material. A lip 44 is formed in the second end 22 of the side 18 to provide increased rigidity in the member 12, maintaining the jaws 30 and 34 of the patient in an open position for easy access. In a preferred embodiment illustrated in FIG. 4, the lip 44 is formed as a rolled edge that generally projects laterally outwardly of side 18, but in other embodiments lip 44 may extend from the second end 22 in any direction, including inwardly.

A flexible sealing element 14 is attached to member 12 so that it covers and seals each aperture 26. Sealing element 14 comprises a first part 46 covering one aperture 26 and a second part 48 covering the other aperture 26. The first part 46 and the second part 48 of the sealing element 14 may be contiguously joined to one another so that the element extends about the bottom portion 16 of the member 12 and extends along the side 18 covering the opposing apertures 26. In an alternative embodiment, the sealing element may comprise two separate parts, with each part 46 and 48 covering a respective aperture 26. In a preferred embodiment, the sealing element is comprised of a foam material having adhesive on opposing faces 50 and 52. Face 52 is then attached by the adhesive to the member 12. Face 50 has a protective layer of stripable material 54 thereon to protect the adhesive until the tooth isolation device 10 is to be used. The sealing element 14 in other embodiments may not include an adhesive on face 52, requiring it to be attached to the member 12 by gluing or any other means well known in the art that is suitable for this purpose. Each part 46 and 48 of the sealing element 14 has a slit 56 formed therethrough that is generally parallel to the edges 36 of the corresponding aperture 26. The slit 56 is generally centered longitudinally between the edges 36 of the corresponding aperture 26 so that the slit 56 is in communication with the aperture 26 and thereby in communication with the interior A of the member 12.

Having thus set forth a preferred construction for the tooth isolation device 10 of this invention, it is to be remembered that this is but a preferred embodiment. Attention is now invited to a description of the use of the tooth isolation device 10 in a preferred embodiment. The member 12 is packaged under generally antiseptic conditions and is manufactured from inexpensive materials so that the tooth isolation device 10 may be used once and then discarded. In other embodiments, the member 12 may be comprised of more sturdy materials that are suitable for sanitizing. Then, all that is required is adding a new sealing element 14 before each use.

In a preferred embodiment, the tooth isolation device is packaged with the sealing element 14 attached to the member 12. Therefore, to use the device 10, the protective cover 54 (shown in FIG. 1) is stripped from each part 46 and 48 of sealing element 14 and then the device 10 is inserted within the patient's mouth so that one aperture 26 is aligned with the lower molars 32 and the other aperture 26 is aligned with the upper molars 28. The patient then closes his/her jaws 30 and 34 on the device 10 so that the molars 28 and 32 project through a slit 56 and its corresponding aperture 26. The eye teeth 40 engage the corresponding concave segment 38, permitting deeper penetration by the molars through the apertures 26. As seen in FIG. 4, with the protective cover 54 removed, the adhesive on face 50 of the sealing element 14 is exposed. As shown in FIG. 5, sealing element 14 may now be pressed against the molars 28 and 32 to provide a tight seal to prevent leakage into and out of the tooth isolation device 10. The sealing element 14 being comprised of a light foam material may be easily formed to the sides of the molars 28 and 32 to fill any gaps. The eye teeth 40 having closed upon the concave segment 38 are held apart by the rigidity of the lip 44 so that the jaws 30 and 34 of the patient are held open. The open second end 22 of member 12 provides easy access to the molars that now extend inwardly into the isolation device 10. After work has been completed upon the molars 28 and 32 the tooth isolation device 10 may be removed and discarded.

It will thus be seen that the objects set forth above among those made apparent from the preceding description are efficiently attained and, since certain changes may be made in the above article without departing from the scope of the invention, it is intended that all matter contained in the above description or shown in the accompanying drawings shall be interpreted as illustrative and not in a limiting sense. It is also to be understood that the following claims are intended to cover all of the generic and specific features of the invention herein described, and all statements of the scope of the invention which, as a matter of language, might be said to fall therebetween.

Now that the invention has been described,

What is claimed is:

1. A tooth isolation device, particularly adapted for use with upper and lower molars, comprising:
 a cup-shaped member comprising a bottom portion and at least one side extending outwardly therefrom to define an open end, said member comprising at least one aperture formed therethrough, said aperture extending from said bottom portion along said side to a point proximal to said open end; and
 a flexible sealing element attached to said member in covering and sealing relation to said aperture, said sealing element comprising a slit formed therethrough in communication with said aperture, whereby said member is adapted to receive at least one molar projecting into said member through said slit and said aperture.

2. A device as in claim 1 wherein said side of said member comprises a first end attached to said bottom portion and a second end spaced apart from said bottom portion, said side further comprising a lip projecting outwardly from said second end of said side.

3. A device as in claim 1 wherein said side of said member is formed from a flexible material.

4. A device as in claim 1 wherein said side of said member comprises two apertures formed therethrough, said apertures generally opposing one another, said sealing element comprising a first part and a second part, said first part in covering and sealing relation with one of said apertures and said second part in covering and sealing relation with the other said aperture, each said port having a slit formed therethrough in communication with its adjacent aperture, whereby said member is adapted to receive at least one upper molar and at least one lower molar projecting into said member through a respective one of said slits and a corresponding one of said apertures.

5. A device as in claim 1 wherein said sealing element comprises two opposing faces, at least one of said faces comprising an adhesive thereon, whereby said adhesive attaches said sealing element to the molar.

6. A device as in claim 1 wherein said sealing element comprises two opposing faces, each of said faces comprising an adhesive thereon, whereby said adhesive on one of said faces attaches said sealing element to said member and said adhesive on the other of said faces is adapted for attachment of said sealing element to the molar projecting through said slit.

7. A device as in claim 1 wherein said slit in said sealing element is longitudinally centered in relation to said at least one aperture in said member.

8. A device as in claim 1 wherein said sealing element comprises a foam material.

9. A device as in claim 1 wherein said side of said member comprises a first end adjacent said bottom portion and a second end spaced apart from said bottom portion, said side further comprising a concave segment extending between said at least one aperture and said second end of said side.

10. A device as in claim 1 wherein said at least one aperture has opposing longitudinal edges, said edges of said at least one aperture curving inwardly.

11. A device as in claim 1 wherein said side of said member is tapered toward said bottom portion, and a circumference of said side adjacent said open end is greater than a circumference of said side adjacent said bottom portion.

* * * * *

UNITED STATES PATENT AND TRADEMARK OFFICE
CERTIFICATE OF CORRECTION

PATENT NO. : 5,340,313
DATED : August 23, 1994
INVENTOR(S) : Gregory J. Hussin

It is certified that error appears in the above-indentified patent and that said Letters Patent is hereby corrected as shown below:

Column 5, claim 4, line 17, delete "port" insert therefore
--part --.

Signed and Sealed this

Eighth Day of November, 1994

Attest:

BRUCE LEHMAN

Attesting Officer     Commissioner of Patents and Trademarks